United States Patent [19]

Beach et al.

[11] 4,293,726

[45] Oct. 6, 1981

[54] PROCESS FOR THE OLIGOMERIZATION OF PROPYLENE AND HIGHER OLEFINS

[75] Inventors: David L. Beach; Thaddeus P. Kobylinski, both of Gibsonia, Pa.

[73] Assignee: Gulf Research & Development Company, Pittsburgh, Pa.

[21] Appl. No.: 151,950

[22] Filed: May 21, 1980

[51] Int. Cl.$^3$ ............................ C07C 2/02; C07C 2/26
[52] U.S. Cl. ...................................... 585/523; 585/511
[58] Field of Search ................................. 585/511, 523

[56] References Cited

U.S. PATENT DOCUMENTS

| | | | |
|---|---|---|---|
| 3,134,824 | 5/1964 | Walker et al. | 585/511 |
| 3,424,816 | 1/1969 | McClure et al. | 585/511 |
| 3,459,826 | 8/1969 | Barnett et al. | 585/511 |
| 3,527,838 | 9/1970 | Barnett et al. | 585/511 |
| 3,530,197 | 9/1970 | McClure | 585/506 |
| 3,532,765 | 10/1970 | Barnett et al. | 585/511 |
| 3,686,159 | 8/1972 | Bauer et al. | 252/431 P |
| 3,736,264 | 5/1973 | Chauvin | 252/429 R |
| 4,024,202 | 5/1977 | Burnham . | |

FOREIGN PATENT DOCUMENTS 1060399 7/1959 Fed. Rep. of Germany .
1033161 6/1966 United Kingdom .

OTHER PUBLICATIONS

Bamford, *J. Polym. Sci., Part C,* No. 4, pp. 1571–1587.
Ichikawa, *J. Chem. Soc. Chem. Comm.,* 1976, pp. 26 & 27.
Bamford et al., *Chem. Abs.* 57, 13961 (1962).
Ichikawa, *J. Chem. Soc., Chem. Comm.,* 1978, pp. 566–567.
Lapidus et al., *Chem. Abs.,* 82, 7897 (1975).
Lapidus et al., *Chem. Abs.,* 85, 3717 (1976).
Smith, *J. Molecular Catalysis* 2, 1977, pp. 229–241.

*Primary Examiner*—Curtis R. Davis
*Attorney, Agent, or Firm*—Deane E. Keith; Forrest D. Stine; Joseph J. Carducci

[57] ABSTRACT

An alpha olefin containing three to 10 carbon atoms, or higher, is oligomerized by intimately contacting the alpha olefin, e.g., in a non-aromatic solvent, with a catalyst produced by contacting (a) a refractory metal oxide/silica support such as alumina/silica wherein the silica content of the support is from about 2 to about 95 weight percent and the metal oxide content of the support is from about 5 to about 98 percent with (b) a tris(cyclopentadienyl)trinickel dicarbonyl. This process is characterized by a relatively high reaction rate at moderate temperatures and pressures and results in the production of significant quantities of dimers, trimers and tetramers.

70 Claims, No Drawings

PROCESS FOR THE OLIGOMERIZATION OF PROPYLENE AND HIGHER OLEFINS

CROSS-REFERENCES TO RELATED APPLICATIONS

Reference is made to applicants' following U.S. applications:

U.S. Patent application Ser. No. 151,948, filed May 21, 1980, entitled "Refractory Metal Oxide/Silica Supported Nickel Cluster Catalyst".

U.S. Patent application Ser. No. 151,961, filed May 21, 1980, entitled "Process for the Oligomerization of Ethylene".

U.S. Patent application Ser. No. 151,953, filed May 21, 1980, entitled "Alkylation of Aromatics with Propylene and Higher Olefins".

U.S. Patent application Ser. No. 151,951, filed May 21, 1980, entitled "Metal Modified Refractory Metal Oxide/Silica Supported Nickel Cluster Catalyst".

U.S. Patent application Ser. No. 151,952, filed May 21, 1980, entitled "Use of Metal Modified Refractory Metal Oxide/Silica Supported Nickel Cluster Catalyst to Oligomerize Ethylene".

The disclosures of the foregoing applications are hereby incorporated by reference.

FIELD OF THE INVENTION

The present invention relates to the use of a refractory metal oxide/silica supported nickel cluster catalyst to oligomerize propylene and higher olefins. More particularly, this invention relates to the use of a catalyst obtained by contacting a refractory metal oxide/silica support with a nickel cluster in the oligomerization of alpha olefins containing three to 10 carbon atoms, or higher.

DESCRIPTION OF THE PRIOR ART

It is well known in the art to use a variety of catalysts to oligomerize ethylene and other lower olefins to higher molecular weight olefins. The term "oligomerize" has been employed, and is employed herein to describe the conversion of lower olefins to olefinic products of higher molecular weight, e.g., to dimer, trimer, tetramer and the like. The reaction rate and product distribution obtained are highly dependent on the exact catalyst composition and the reaction conditions employed. Two such general classes of catalysts are the "Ziegler" types consisting of aluminum trialkyls and the "Ziegler-Natta" types consisting of aluminum alkyl halides and titanium halides. A major disadvantage of aluminum alkyl catalysts is their highly reactive and pyrophoric nature.

Several heterogeneous supported cyclopentadienyl nickel catalysts have been employed to oligomerize lower olefins to higher molecular weight olefins. One such process described in U.S. Pat. No. 3,459,826 to Barnett et employs nickelocene, i.e., bis(cyclopentadienyl)nickel, and an inorganic oxide catalyst support. This process, however, requires pretreatment with elemental hydrogen and yields 84% dimer and trimer. A related process using (π-cyclopentenyl)cyclopentadienyl-nickel is described in U.S. Pat. No. 3,532,765 to Barnett et al.

A non-pyrophoric nickel-supported catalyst is described by Masaru Ichikawa in an article entitled "Preparation and Catalytic Activities of Supported Nickel Clusters on a Silica Surface", *J. Chem. Soc., Chem. Comm.* (1976), pages 26 and 27. This article discloses tris(cyclopentadienyl)trinickel dicarbonyl and other nickel cluster compounds deposited on silica gel or Vycor glass No. 7930 followed by heating at 120° C. as catalysts for olefin hydrogenation and for the "oxo" reaction. Vycor glass No. 7930 is understood to be 95.6 weight percent silica, 1.0 weight percent alumina, 2.25 weight percent boric acid, the remaining 0.25 weight percent being unidentified contaminants.

SUMMARY OF THE INVENTION

It has now been found that alpha olefins containing three to 10 carbon atoms, or higher, can be oligomerized to higher olefins, by intimately contacting the alpha olefin, e.g., in a non-aromatic solvent, with a catalyst produced by contacting (a) a refractory metal oxide/silica support such as alumina/silica wherein the silica content of the support is from about 2 to about 95 weight percent and the metal oxide content of the support is from about 5 to about 98 percent with (b) a tris(cyclopentadienyl)trinickel dicarbonyl. The process is characterized by ease of catalyst handling, high activity and low operating temperatures and pressures, and the production of significant amounts of dimers, trimers and tetramers.

The tris(cyclopentadienyl)trinickel dicarbonyl used herein has the structure:

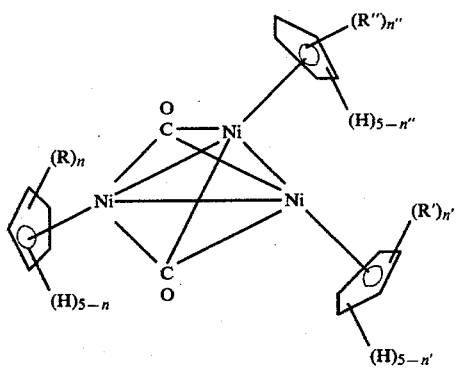

wherein R, R' and R" can be the same or different $C_1$ to $C_{20}$ inclusive, hydrocarbon radicals, and n, n' and n" can be the same or different integers of 0 to 5, inclusive. The R, R' and R" hydrocarbon radicals can be saturated or unsaturated, they can include aliphatic, alicyclic and aromatic radicals such as methyl, ethyl, propyl, butyl, pentyl, cyclopentyl, cyclohexyl, allyl, phenyl and naphthyl radicals. One or more of the cyclopentadienyl moieties in the foregoing tris(cyclopentadienyl)trinickel dicarbonyl can be substituted so as to form an indenyl moiety or a fluorenyl moiety.

Specific examples of nickel clusters which can be used include:
tris(cyclopentadienyl)trinickel dicarbonyl,
tris(methylcyclopentadienyl)trinickel dicarbonyl, (methylcyclopentadienyl)bis(cyclopentadienyl)trinickel dicarbonyl,
bis(methylcyclopentadienyl)(cyclopentadienyl)-trinickel dicarbonyl,
tris(pentamethylcyclopentadienyl)trinickel dicarbonyl,
(pentamethylcyclopentadienyl)bis(cyclopentadienyl)-trinickel dicarbonyl, bis(pentamethylcyclopentadienyl)(cyclopentadienyl)-trinickel dicarbonyl,
(methylcyclopentadienyl)bis(pentamethylcyclopentadienyl)trinickel dicarbonyl,
bis(methylcyclopentadienyl)(pentamethylcyclopentadienyl)trinickel dicarbonyl,
tris(ethylcyclopentadienyl)trinickel dicarbonyl,
(ethylcyclopentadienyl)bis(cyclopentadienyl)trinickel dicarbonyl,
bis(ethylcyclopentadienyl)(cyclopentadienyl)trinickel dicarbonyl,
tris(n-propylcyclopentadienyl)trinickel dicarbonyl,
tris(iso-propylcyclopentadienyl)trinickel dicarbonyl,
tris(butylcyclopentadienyl)trinickel dicarbonyl,
tris(pentylcyclopentadienyl)trinickel dicarbonyl,
tris(indenyl)trinickel dicarbonyl,
(indenyl)bis(cyclopentadienyl)trinickel dicarbonyl,
bis(indenyl)(cyclopentadienyl)trinickel dicarbonyl,
(indenyl)bis(methylcyclopentadienyl)trinickel dicarbonyl,
bis(indenyl)(methylcyclopentadienyl)trinickel dicarbonyl,
(indenyl)bis(pentamethylcyclopentadienyl)trinickel dicarbonyl,
bis(indenyl)(pentamethylcyclopentadienyl)trinickel dicarbonyl,
wherein the indenyl moiety has the structure:

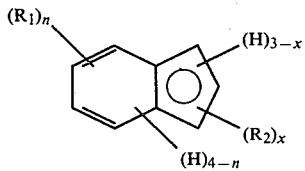

wherein $(R_1)$ and $(R_2)$ are the same or different $C_1$ to to $C_{10}$ hydrocarbon radicals, n is an integer of 0 to 4, and x is an integer of 0 to 3,
tris(fluorenyl)trinickel dicarbonyl,
(fluorenyl)bis(cyclopentadienyl)trinickel dicarbonyl,
bis(fluorenyl)(cyclopentadienyl)trinickel dicarbonyl,
(fluorenyl)bis(methylcyclopentadienyl)trinickel dicarbonyl,
bis(fluorenyl)methylcyclopentadienyl)trinickel dicarbonyl,
(fluorenyl)bis(pentamethylcyclopentadienyl)trinickel dicarbonyl,
bis(fluorenyl)(pentamethylcyclopentadienyl)trinickel dicarbonyl,
wherein the fluorenyl moiety has the structure:

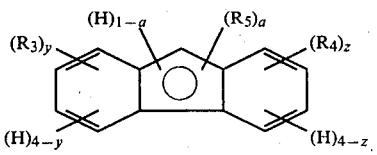

wherein $(R_3)$, $(R_4)$ and $(R_5)$ can be the same or different $C_1$ to $C_{10}$ hydrocarbon radicals; y and z can be the same or different integers of 0 to 4; and a is 0 or 1. The $(R_1)$, $(R_2)$, $(R_3)$, $(R_4)$ and $(R_5)$ hydrocarbon radicals can be the same or different, saturated or unsaturated and include the hydrocarbon radicals as described for R, R' and R".

The metal oxide associated with the silica in the support may be defined by the formula $M_xO_y$ wherein M is aluminum, magnesium, zirconium or thorium, x is an integer of from 1 to 2 and y is an integer of from 1 to 3. Specific examples of such compounds include $Al_2O_3$, $MgO$, $ZrO_2$, $ThO_2$, etc.

DESCRIPTION OF THE PREFERRED EMBODIMENTS

The alpha olefins containing three to 10 carbon atoms, or higher, which can be oligomerized in accordance with the practice of this invention include propylene, 1-butene, 1-hexene, 1-octene, 1-decene, and the like. In oligomerizing the alpha olefin with the catalyst defined herein, the alpha olefin and catalyst are contacted with each other at a temperature in the range of about 20° to about 250° C., preferably about 5° to about 170° C., and a pressure of about one to about 50 atmospheres, preferably from about one to about 30 atmospheres, for about 10 minutes to about 12 hours, or longer, but preferably about 0.5 to about four hours. Thus, the alpha olefin can be brought into contact with a slurry composed of said catalyst and a non-aromatic hydrocarbon solvent as defined hereinafter. The amount of catalyst required can range from about 0.1 milligram to about 1.0 gram of nickel in the catalyst per mole of the alpha olefin, preferably from about 1.0 milligram to about 0.1 gram of nickel in the catalyst per mole of the alpha olefin.

A critical feature of this invention resides in the use of a non-aromatic solvent, that is, aliphatic and alicyclic solvents. Aliphatic solvents that can be used can have from four to 14 carbon atoms, or even higher, preferably from five to 10 carbon atoms. Alicyclic solvents that can be used can have from five to 14 carbon atoms, or even higher, preferably from five to 10 carbon atoms. Specific examples of such solvents that can be used include isobutane, n-pentane, isopentane, n-hexane, isohexane, dimethylbutane, n-heptane, methylhexane, n-octane, isooctane, n-nonane, n-decane, n-dodecane, cyclopentane, methylcyclopentane, cyclohexane, methylcyclohexane, ethylcyclohexane, cycloheptane, cyclooctane, cyclononane, cyclodecane, etc. The amount of solvent used can vary over wide limits, for example, on a volume basis, from about 10 to about 150 milliliters, or more, per mole of alpha olefin, preferably from about 25 to about 100 milliliters per mole of alpha olefin. If the reactant olefin is a liquid under the reaction conditions, it is obvious that no solvent is necessary, although a solvent, such as defined above, can be used if desired. When the nickel supported catalyst is contacted with an alpha olefin containing three or more carbon atoms under the conditions defined above in an aromatic solvent, such as benzene, alkylation of the solvent is the dominant reaction.

The nickel cluster has a low solubility in certain aliphatic and alicyclic solvents, such as heptane. Thus, it is preferred to prepare the catalyst in situ in the oligomerization reactor by charging the nickel cluster as a solid to the reactor along with the metal oxide/silica support, adding the non-aromatic solvent, which is also a solvent for the oligomerization reaction, and, after the nickel cluster has been deposited on the support, adding the alpha olefin to the reactor.

The supported nickel catalyst and the alpha olefin can be contacted in any suitable reaction vessel such as an autoclave or similar reaction vessel provided with suitable agitation means. Preferably, the reaction vessel is purged with an inert gas such as argon or nitrogen before the catalyst and alpha olefin are added.

At the end of the reaction period, the contents of the reaction vessel are cooled to a temperature of about −10° to about 50° C., preferably about 20° to about 50° C., after which any unreacted propylene or butene, if present, are vented from the system and the pressure is reduced to about one to about five atmospheres. The reactor contents are then filtered to recover the solid catalyst. The solvent and the alpha olefin oligomers can be separated and isolated, if desired, by conventional methods, such as fractional distillation, extraction, selective adsorption, etc. The reaction solvent, catalyst and any unreacted alpha olefin can be recycled to the reaction vessel.

A suitable support for the catalyst composition for use in the process of this invention is a metal oxide/silica support wherein the silica content is from about 2 to about 95 weight percent and the metal oxide content is from about 5 to about 98 weight percent. Preferably, the support comprises from about 15 to about 92 weight percent silica and about 10 to about 85 weight percent metal oxide; and most preferably from about 80 to about 92 weight percent silica and from about 10 to about 20 weight percent metal oxide. The metal oxide/silica supports include synthetic materials as well as acid-treated clays or even the crystalline alumina silicates known as molecular sieves, so long as the silica and alumina contents are within the ranges specified. Thus, any of the commercially available metal oxide/silicas having the proper silica to metal oxide ratios can suitably be used to prepare the compositions of this invention. The preferred alumina/silicas are coprecipitated from aqueous or alcoholic solutions of a silicate such as sodium silicate or silicic acid and an aluminum salt such as aluminum nitrate, aluminum sulfate or aluminum chloride. For example, an aqueous solution of silicic acid and aluminum nitrate produces a coprecipitate when treated with ammonium hydroxide at a controlled pH of about 8. Differing physical properties of the coprecipitates result by varying the pH during precipitation. The precipitates are an intimate comixture of silicon and aluminum oxides.

Preferably, the support is calcined prior to contact with the nickel cluster as by heating at a temperature of from about 200° C. to about 800° C. and, more preferably, from about 450° C. to about 650° C. for a period of from about one to about 24 hours, or even longer, but preferably about four to about 12 hours. The calcining operation can be conducted in air, but is preferably conducted in an inert atmosphere such as in a stream of argon or nitrogen. Following the calcining operation, the support is cooled slowly in an inert atmosphere and stored in the absence of air.

The calcined support is then contacted in the absence of air with the nickel cluster, that is, a tris(cyclopentadienyl)trinickel dicarbonyl. The nickel cluster defined by the chemical formula $(\eta^5\text{-}C_5H_5)_3Ni_3(CO)_2$, wherein $\eta$ is the Greek letter eta, used herein, can be prepared by the method of E. O. Fischer et al described in *Chem. Ber.*, 91, 1725 (1958). This compound is a solid at room temperature and is not sensitive to air. The structure of the nickel cluster consists of a triangle of nickel atoms with a cyclopentadienyl ligand bonded to each nickel in a pentahapto fashion and two triply-bridging carbon monoxide ligands. This complex has the structure represented above when each of n, n' and n" has a value of O.

One method of contacting the support with the nickel cluster is to use a solution of the nickel cluster in a liquid hydrocarbon solvent which is non-reactive. Examples of such solvents include pentane, hexane, heptane, cyclopentane, cyclohexane, benzene, toluene, and xylene. The amount of nickel cluster used is not critical and can vary widely as long as the nickel content of the product obtained from the reaction of the nickel cluster with the support is within the range of about 0.001 to above five weight percent, preferably within the range of about 0.05 to about two weight percent.

The nickel cluster and the support are contacted at a temperature of from about 20° to about 200° C. for a period of about 10 minutes to about 12 hours and, more preferably, for about 15 minutes to about one hour at a temperature of from about 20° to about 100° C. The temperature and time can vary widely depending upon the solubility-temperature profile of the solvent and nickel cluster. They can be contacted in any suitable reaction vessel such as an autoclave.

As previously mentioned, the nickel cluster has a low solubility in certain aliphatic and alicyclic solvents such as heptane and cyclohexane. This may result in a very slow transfer and/or an incomplete transfer of the nickel cluster from solution to the support. Thus, when using such solvents, a different method of contacting the nickel cluster and the support is preferably used. According to this method, instead of adding the nickel cluster as a solution to the reaction chamber, it is charged as a solid with the support. After purging the reaction chamber with an inert gas such as argon or nitrogen, the solvent is then added to the reaction chamber.

Following the necessary contact time to effect deposition of the nickel cluster onto the support, the resultant catalyst composition can be separated from the solvent diluent and stored, preferably in an inert atmosphere, until ready for use. Separation can be accomplished by conventional techniques such as filtration, centrifugation, and decantation. The catalyst composition can be dried in an inert atmosphere. Alternatively, the catalyst composition can be used to oligomerize the alpha olefin in the solvent diluent in which it was prepared if a non-aromatic solvent diluent was used.

It is preferred to activate or preactivate the catalyst composition prior to contact with the alpha olefin unless temperatures exceeding 100° C. were used in the reaction of the nickel cluster with the support in which case the activation or preactivation is unnecessary. Activation and preactivation of the catalyst can be accomplished by heating it in an inert atmosphere at a temperature between about 70° and about 200° C., preferably between about 100° to about 170° C., for from about five minutes to about 4 hours, or longer, but preferably about 20 minutes to about one hour. The term "activation" as used herein refers to an operation performed in situ in the oligomerization reactor prior to the addition of the alpha olefin; and the term "preactivation" refers to an operation performed external to the oligomerization reactor.

The use of the catalyst compositions in the process of this invention results in several advantages over prior art ethylene oligomerization catalysts. Thus, their use in the oligomerization of an alpha olefin avoids the use of the highly reactive, pyrophoric aluminum alkyls. Nickel oligomerization catalysts ordinarily do not result in the production of significant amounts of higher olefins than dimers. The catalyst described herein, however, when used to oligomerize an alpha olefin results in the production of significant amounts of oligomers higher than dimers, that is, oligomers having up to about 20 carbon atoms. Moreover, higher reaction rates are attained at lower temperatures and pressures than with prior art catalysts.

The following examples illustrate the best mode contemplated for carrying out this invention. The activities reported were calculated based upon the weight of elemental nickel supplied by the nickel complex. All percentages are by weight unless otherwise indicated.

EXAMPLE 1

An alumina/silica support comprising 87 weight percent silica and 12 weight percent alumina was calcined under argon at 550° C. for 5 hours. The support had a surface area of 425–450 m.$^2$/g. Subsequently, 2.0 grams of this support and 0.0100 gram of solid tris(cyclopentadienyl)trinickel dicarbonyl under argon were charged to a 300 cc. autoclave. Purging was accomplished with 3 successive pressure-vent cycles using argon. Cyclohexane (50 ml.) was weighed and syringed into the autoclave under argon. The contents were stirred at ambient temperature for 2.0 hours and were then rapidly heated to 150° C. and maintained at that temperature for 30 minutes. Propylene was then added to a total pressure of 100 psig (690 kPa) and maintained at this temperature for 1.0 hour. The autoclave was then rapidly cooled to 5° C. and the pressure reduced to atmospheric. The liquid contents were collected in a tared, cooled bottle and analyzed immediately by gas chromatography. The results of these experiments are shown in Table I. An activity of 613 grams of oligomer per gram of nickel per hour was found.

TABLE I

| Selectivity, percent | |
|---|---|
| C-6 olefins | 52 |
| C-9 olefins | 42 |
| C-12 olefins | 6 |

Thus, it is seen from Table I that significant amounts of propylene dimers and trimers are produced.

EXAMPLE 2

For comparative purposes, the procedure of Example 1 was repeated substituting benzene for cyclohexane and using 2.68 grams of the support and 0.0077 gram of tris(cyclopentadienyl)trinickel dicarbonyl. The results are set forth in Table II below:

TABLE II

| Selectivity, percent | |
|---|---|
| C-6 olefins | 1 |
| C-9 olefins | 0.5 |
| Cumene | 26.5 |
| Diisopropylbenzenes | 37 |
| ≧C-12 (olefins plus alkylated benzenes, excluding diisopropylbenzenes) | 35.5 |

It will be seen from Table II that when the reaction was run in benzene, alkylation was the dominant reaction, rather than olefin oligomerization.

EXAMPLE 3

The process of Example 1 was repeated substituting 1-hexene for propylene at one atmosphere. The oligomerization reaction was run for 1.4 hours. The results of analysis of the product obtained are reported in Table III. An activity of 1552 grams of oligomer per gram of nickel per hour was observed.

TABLE III

| Selectivity, percent | |
|---|---|
| C-12 olefins | 78 |
| C-18 olefins | 17 |
| C-24 olefins | 4 |
| C-30 olefins | 1 |

Thus, it is seen that the 1-hexene is oligomerized to provide significant amounts of dimers and trimers.

EXAMPLE 4

Example 3 was repeated substituting benzene for cyclohexane and using 2.42 grams of the support and a run time of 4.7 hours. The results set forth in Table IV, below, were obtained:

TABLE IV

| Selectivity, percent | |
|---|---|
| C-12 olefins | 12 |
| 3-phenylhexane | 23 |
| 2-phenylhexane | 41 |
| (C-12)-benzene | 6 |
| ≧C-18 (olefins + alkylated benzenes) | 18 |

Again, it is seen that when the reaction is run in benzene, alkylation was the dominant reaction, rather than olefin oligomerization.

Although the invention has been described in considerable detail with particular reference to certain preferred embodiments thereof, variations and modifications can be effected within the spirit and scope of the invention as described hereinbefore, and as defined in the appended claims.

We claim:

1. A process for oligomerizing an alpha olefin which comprises contacting an alpha olefin having at least three carbon atoms with a catalyst composition obtained by contacting (a) a refractory metal oxide/silica support wherein the silica content of said support is from about 2 to about 95 weight percent and the metal oxide content of said support is from about 5 to about 98 weight percent with (b) a tris(cyclopentadienyl)-trinickel dicarbonyl.

2. A process as defined in claim 1 wherein said tris(cyclopentadienyl)trinickel dicarbonyl has the structure:

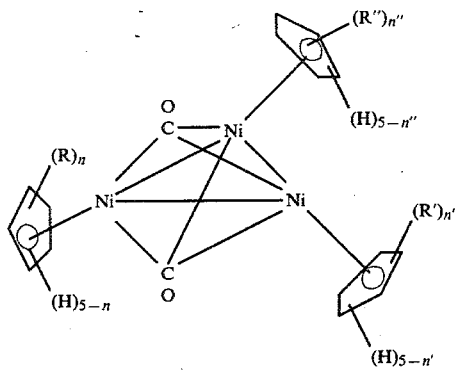

wherein R, R' and R" are the same or different $C_1$ to $C_{20}$ hydrocarbon radicals and n, n' and n" can be the same or different integers of 0 to 5, inclusive.

3. A process as defined in claim 2 wherein the metal oxide component of said support has the formula $M_xO_y$, wherein M is aluminum, magnesium, zirconium or thorium, x is an integer of from 1 to 2 and y is an integer of from 1 to 3.

4. A process as defined in claim 3 wherein the metal oxide in said support is alumina.

5. A process as defined in claim 1 wherein the silica content in said support is from about 15 to about 92 weight percent and the metal oxide content in said support is from about 10 to about 85 weight percent.

6. A process as defined in claim 1 wherein the silica content in said support is from about 80 to about 92 weight percent and the metal oxide content in said support is from about 10 to about 20 weight percent.

7. A process as defined in claim 4 wherein the silica content in said support is from about 15 to about 92 weight percent and the alumina content in said support is from about 10 to about 85 weight percent.

8. A process as defined in claim 4 wherein the silica content in said support is from about 80 to about 92 weight percent and the alumina content in said support is from about 10 to about 20 weight percent.

9. A process as defined in claim 4 wherein the silica content in said support is about 87 weight percent and the alumina content in said support is about 12 weight percent.

10. A process as defined in claim 4 wherein the silica content in said support is about 75 weight percent and the alumina content in said support is about 25 weight percent.

11. A process as defined in claim 1 wherein said tris(cyclopentadienyl)trinickel dicarbonyl is defined by the chemical formula $(\eta^5\text{-}C_5H_5)_3Ni_3(CO)_2$.

12. A process as defined in claim 2 wherein said tris(cyclopentadienyl)trinickel dicarbonyl is defined by the chemical formula $(\eta^5\text{-}C_5H_5)_3Ni_3(CO)_2$.

13. A process as defined in claim 3 wherein said tris(cyclopentadienyl)trinickel dicarbonyl is defined by the chemical formula $(\eta^5\text{-}C_5H_5)_3Ni_3(CO)_2$.

14. A process as defined in claim 4 wherein said tris(cyclopentadienyl)trinickel dicarbonyl is defined by the chemical formula $(\eta^5\text{-}C_5H_5)_3Ni_3(CO)_2$.

15. A process as defined in claim 5 wherein said tris(cyclopentadienyl)trinickel dicarbonyl is defined by the chemical formula $(\eta^5\text{-}C_5H_5)_3Ni_3(CO)_2$.

16. A process as defined in claim 6 wherein said tris(cyclopentadienyl)trinickel dicarbonyl is defined by the chemical formula $(\eta^5\text{-}C_5H_5)_3Ni_3(CO)_2$.

17. A process as defined in claim 7 wherein said tris(cyclopentadienyl)trinickel dicarbonyl is defined by the chemical formula $(\eta^5\text{-}C_5H_5)_3Ni_3(CO)_2$.

18. A process as defined in claim 8 wherein said tris(cyclopentadienyl)trinickel dicarbonyl is defined by the chemical formula $(\eta^5\text{-}C_5H_5)_3Ni_3(CO)_2$.

19. A process as defined in claim 9 wherein said tris(cyclopentadienyl)trinickel dicarbonyl is defined by the chemical formula $(\eta^5\text{-}C_5H_5)_3Ni_3(CO)_2$.

20. A process as defined in claim 10 wherein said tris(cyclopentadienyl)trinickel dicarbonyl is defined by the chemical formula $(\eta^5\text{-}C_5H_5)_3Ni_3(CO)_2$.

21. A process as defined in claim 1 wherein said support is calcined, prior to said contact with said tris(cyclopentadienyl)trinickel dicarbonyl at a temperature from about 200° to about 800° C. for about one to about 24 hours.

22. A process as defined in claim 1 wherein said contact between said support and said tris(cyclopentadienyl)trinickel dicarbonyl is conducted in the absence of air at a temperature of about 20° to about 200° C.

23. A process as defined in claim 1 wherein a solution of said tris(cyclopentadienyl)trinickel dicarbonyl is contacted with said support.

24. A process as defined in claim 23 wherein said solution is a benzene solution.

25. A process as defined in claim 23 wherein said solution is a cyclohexane solution.

26. A process as defined in claim 1 wherein the nickel content of said catalyst composition is from about 0.001 to about five weight percent.

27. A process as defined in claim 1 wherein the nickel content of said catalyst composition is from about 0.05 to about two weight percent.

28. A process as defined in claim 14 wherein the nickel content of said catalyst composition is from about 0.001 to about five weight percent.

29. A process as defined in claim 14 wherein the nickel content of said catalyst composition is from about 0.05 to about two weight percent.

30. A process as defined in claim 1 wherein said contact between said support and said tris(cyclopentadienyl)trinickel dicarbonyl is effected at a temperature from about 20° to about 200° C. for about 10 minutes to about 12 hours.

31. A process as defined in claim 1 wherein said contact between said support and said tris(cyclopentadienyl)trinickel dicarbonyl is effected at a temperature from about 20° to about 100° C. for about 15 minutes to about one hour.

32. A process as defined in claim 14 wherein said contact between said support and said tris(cyclopentadienyl)trinickel dicarbonyl is effected at a temperature from about 20° to about 200° C. for about 10 minutes to about 12 hours.

33. A process as defined in claim 14 wherein said contact between said support and said tris(cyclopentadienyl)trinickel dicarbonyl is effected at a temperature from about 20° to about 100° C. for about 15 minutes to about one hour.

34. A process as defined in claim 1 wherein the solid tris(cyclopentadienyl)trinickel dicarbonyl is contacted with said support and a hydrocarbon solvent is then added.

35. A process as defined in claim 34 wherein said hydrocarbon solvent is benzene.

36. A process as defined in claim 34 wherein said hydrocarbon solvent is cyclohexane.

37. A process as defined in claim 1 wherein said catalyst is activated or preactivated by heating at a temperature of about 70° to about 200° C. for about five minutes to about four hours.

38. A process as defined in claim 1 wherein said catalyst is activated or preactivated by heating at a temperature of about 100° to about 170° C. for about twenty minutes to about one hour.

39. A process as defined in claim 14 wherein said catalyst is activated or preactivated by heating at a temperature of about 70° to about 200° C. for about five minutes to about four hours.

40. A process as defined in claim 14 wherein said catalyst is activated or preactivated by heating at a temperature of about 100° to about 170° C. for about twenty minutes to about one hour.

41. A process as defined in claim 1 wherein said alpha olefin and catalyst composition are contacted at a temperature of from about 20° to about 250° C. and a pressure of from about one to about 50 atmospheres for about 10 minutes to about 12 hours.

42. A process as defined in claim 1 wherein said alpha olefin and catalyst composition are contacted at a temperature of from about 50° to about 170° C. and a pressure of from about one to about 30 atmospheres for about 0.5 to about four hours.

43. A process as defined in claim 4 wherein said alpha olefin and catalyst composition are contacted at a temperature of from about 20° to about 250° C. and a pressure of from about one to about 50 atmospheres for about 10 minutes to about 12 hours.

44. A process as defined in claim 4 wherein said alpha olefin and catalyst composition are contacted at a temperature of from about 50° to about 170° C. and a pressure of from about one to about 30 atmospheres for about 0.5 to about four hours.

45. A process as defined in claim 14 wherein said alpha olefin and catalyst composition are contacted at a temperature of from about 20° to about 250° C. and a pressure of from about one to about 50 atmospheres for about 10 minutes to about 12 hours.

46. A process as defined in claim 14 wherein said alpha olefin and catalyst composition are contacted at a temperature of from about 50° to about 170° C. and a pressure of from about one to about 30 atmospheres for about 0.5 to about four hours.

47. A process as defined in claim 1 wherein said alpha olefin contains three to 10 carbon atoms.

48. A process as defined in claim 47 wherein said alpha olefin is propylene.

49. A process as defined in claim 47 wherein said alpha olefin is 1-hexene.

50. A process as defined in claim 4 wherein said alpha olefin contains three to 10 carbon atoms.

51. A process as defined in claim 50 wherein said alpha olefin is propylene.

52. A process as defined in claim 50 wherein said alpha olefin is 1-hexene.

53. A process as defined in claim 14 wherein said alpha olefin contains three to 10 carbon atoms.

54. A process as defined in claim 53 wherein said alpha olefin is propylene.

55. A process as defined in claim 53 wherein said alpha olefin is 1-hexene.

56. A process as defined in claim 1 wherein said alpha olefin and catalyst composition are contacted in the presence of a non-aromatic solvent.

57. A process as defined in claim 56 wherein said solvent is an aliphatic solvent.

58. A process as defined in claim 56 wherein said solvent is an alicyclic solvent.

59. A process as defined in claim 4 wherein said alpha olefin and catalyst composition are contacted in the presence of a non-aromatic solvent.

60. A process as defined in claim 59 wherein said solvent is an aliphatic solvent.

61. A process as defined in claim 59 wherein said solvent is an alicyclic solvent.

62. A process as defined in claim 14 wherein said alpha olefin and catalyst composition are contacted in the presence of a non-aromatic solvent.

63. A process as defined in claim 62 wherein said solvent is an aliphatic solvent.

64. A process as defined in claim 62 wherein said solvent is an alicyclic solvent.

65. A process as defined in claim 1 wherein said catalyst composition is present in an amount sufficient to provide about 0.1 mg. to about 1.0 g. of nickel per mole of alpha olefin.

66. A process as defined in claim 1 wherein said catalyst composition is present in an amount sufficient to provide about 1.0 mg. to about 0.1 g. of nickel per mole of alpha olefin.

67. A process as defined in claim 4 wherein said catalyst composition is present in an amount sufficient to provide about 0.1 mg. to about 1.0 g. of nickel per mole of alpha olefin.

68. A process as defined in claim 4 wherein said catalyst composition is present in an amount sufficient to provide about 1.0 mg. to about 0.1 g. of nickel per mole of alpha olefin.

69. A process as defined in claim 14 wherein said catalyst composition is present in an amount sufficient to provide about 0.1 mg. to about 1.0 g. of nickel per mole of alpha olefin.

70. A process as defined in claim 14 wherein said catalyst composition is present in an amount sufficient to provide about 1.0 mg. to about 0.1 g. of nickel per mole of alpha olefin.

* * * * *

UNITED STATES PATENT AND TRADEMARK OFFICE
CERTIFICATE OF CORRECTION

PATENT NO. : 4,293,726

DATED : October 6, 1981

INVENTOR(S) : David L. Beach and Thaddeus P. Kobylinski

It is certified that error appears in the above-identified patent and that said Letters Patent are hereby corrected as shown below:

Column 4, line 14, "5°" should read --50°--;
            line 56, "in situ" should read --in situ--.

Column 6, line 6, "above" should read --about--;
            line 53, "in" should read --in--;
            line 54, "situ" should read --situ--.

Signed and Sealed this

Twenty-third Day of November 1982

[SEAL]

Attest:

GERALD J. MOSSINGHOFF

Attesting Officer    Commissioner of Patents and Trademarks